US00PP29209P2

(12) United States Plant Patent
Bisschop et al.

(10) Patent No.: US PP29,209 P2
(45) Date of Patent: Apr. 3, 2018

(54) ***RUDBECKIA* PLANT NAMED 'ET RDB 401'**

(50) Latin Name: ***Rudbeckia* hybrid**
Varietal Denomination: ET RDB 401

(71) Applicants: Elisabeth Bisschop, Boijl (NL); Bart Noordhuis, Boijl (NL)

(72) Inventors: Elisabeth Bisschop, Boijl (NL); Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 36 days.

(21) Appl. No.: 15/330,384

(22) Filed: Sep. 13, 2016

(51) Int. Cl.
*A01H 5/02* (2006.01)

(52) U.S. Cl.
USPC ..... Plt./474; Plt./428

(58) Field of Classification Search
USPC ..... Plt./474, 428, 263.1
CPC ..... A01H 5/025; A01H 5/02; A01H 5/00
See application file for complete search history.

*Primary Examiner* — June Hwu
(74) *Attorney, Agent, or Firm* — C. A. Whealy

(57) ABSTRACT

A new and distinct cultivar of *Rudbeckia* plant named 'ET RDB 401', characterized by its compact, upright to outwardly spreading and mounded plant habit; freely branching growth habit; relatively small leaves; freely flowering habit; single-type inflorescences with yellow and dark reddish brown bi-colored ray florets positioned above the foliar plane on strong peduncles; and good postproduction longevity.

2 Drawing Sheets

Botanical designation: *Rudbeckia* hybrid.
Cultivar denomination: 'ET RDB 401'.

BACKGROUND OF THE INVENTION

The present invention relates to a new and distinct cultivar of *Rudbeckia* plant, botanically known as *Rudbeckia* hybrid and hereinafter referred to by the name 'ET RDB 401'.

The new *Rudbeckia* plant is a product of a planned breeding program conducted by the Inventors in Boijl, The Netherlands. The objective of the breeding program is to create new compact *Rudbeckia* plants with small leaves and attractive long-lasting inflorescences supported by strong peduncles.

The new *Rudbeckia* plant originated from a cross-pollination made by the Inventors in Boijl, The Netherlands in 2012 of a proprietary selection of *Rudbeckia hirta*×*Echinacea purpurea* identified as code number 16-0336, not patented, as the female, or seed parent with a proprietary selection of *Rudbeckia hirta* identified as code number 01-2426, not patented, as the male, or pollen, parent. The new *Rudbeckia* plant was discovered and selected by the Inventor as a single flowering plant from within the progeny of the stated cross-pollination in a controlled environment in Boijl, The Netherlands in 2013.

Asexual reproduction of the new *Rudbeckia* by tissue culture in a controlled greenhouse environment in Boijl, The Netherlands since 2013 has shown that the unique features of this new *Rudbeckia* are stable and reproduced true to type in successive generations.

SUMMARY OF THE INVENTION

Plants of the new *Rudbeckia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET RDB 401'. These characteristics in combination distinguish 'ET RDB 401' as a new and distinct *Rudbeckia* plant:

1. Compact, upright to outwardly spreading and mounded plant habit.
2. Freely branching growth habit.
3. Relatively small leaves.
4. Freely flowering habit.
5. Single-type inflorescences with yellow and dark reddish brown bi-colored ray florets positioned above the foliar plane on strong peduncles.
6. Good postproduction longevity.

Plants of the new *Rudbeckia* differ from plants of the female parent selection in the following characteristics:

1. Plants of the new *Rudbeckia* are more compact and denser than plants of the female parent selection.
2. Inflorescences of plants of the new *Rudbeckia* are longer lasting than inflorescences of plants of the female parent selection.

Plants of the new *Rudbeckia* differ from plants of the male parent selection in the following characteristics:

1. Plants of the new *Rudbeckia* are more compact and denser than plants of the male parent selection.
2. Inflorescences of plants of the new *Rudbeckia* are longer lasting than inflorescences of plants of the male parent selection.

Plants of the new *Rudbeckia* can be compared to *Rudbeckia hirta*×*Echinacea purpurea* 'ET-RDB 03', disclosed in U.S. Plant Pat. No. 25,206. Plants of the new *Rudbeckia* differ primarily from plants of 'ET-RDB 03' in the following characteristics:

1. Plants of the new *Rudbeckia* are more compact than plants of 'ET-RDB 03'.

2. Plants of the new *Rudbeckia* are more freely flowering than plants of 'ET-RDB 03'.
3. Plants of the new *Rudbeckia* and 'ET-RDB 03' differ in ray floret color as plants of 'ET-RDB 03' have dark reddish bronze-colored ray florets.

Plants of the new *Rudbeckia* can be compared to *Rudbeckia hirta×Echinacea purpurea* 'ET-RDB 01', disclosed in U.S. Plant Pat. No. 25,221. Plants of the new *Rudbeckia* differ primarily from plants of 'ET-RDB 01' in the following characteristics:

1. Plants of the new *Rudbeckia* are shorter than plants of 'ET- RDB 01'.
2. Plants of the new *Rudbeckia* and 'ET-RDB 01' differ in ray floret color as plants of 'ET-RDB 01' have more reddish-colored ray florets.

BRIEF DESCRIPTION OF THE PHOTOGRAPHS

The accompanying photographs illustrate the overall appearance of the new *Rudbeckia* showing the colors as true as it is reasonably possible to obtain in colored reproductions of this type. Colors in the photographs may differ slightly from the color values cited in the detailed botanical description which accurately describe the colors of the new *Rudbeckia*.

The photograph on the first sheet comprises a side perspective view of a typical flowering plant of 'ET RDB 401' grown in a container.

The photograph on the second sheet is a close-up view of a typical inflorescence of 'ET RDB 401'.

DETAILED BOTANICAL DESCRIPTION

The aforementioned photographs and following observations, measurements and values describe plants grown in 2.5-liter containers during the spring in an outdoor nursery in Boijl, The Netherlands and under cultural conditions typical of commercial *Rudbeckia* production. During the production of the plants, day temperatures averaged 16° C. and night temperatures averaged 10° C. Plants were 15 weeks old when the photographs and the detailed description were taken. In the following description, color references are made to The Royal Horticultural Society Colour Chart, 2001 Edition, except where general terms of ordinary dictionary significance are used.

Botanical classification: *Rudbeckia* hybrid 'ET RDB 401'.

Parentage:

*Female, or seed, parent*.—Proprietary selection of *Rudbeckia hirta×Echinacea purpurea* identified as code number 16-0336, not patented.

*Male, or pollen, parent*.—Proprietary selection of *Rudbeckia hirta* identified as code number 01-2426, not patented.

Propagation:

*Type*.—By tissue culture.

*Time to initiate roots*.—About seven to eight days at soil temperatures about 15° C. and ambient temperatures about 20° C.

*Time to produce a rooted young plants*.—About four weeks at soil temperatures about 15° C. and ambient temperatures about 20° C.

*Root description*.—Medium in thickness; fleshy; color, close to 162C.

*Rooting habit*.—Freely branching; medium density.

Plant description:

*Plant and growth habit*.—Herbaceous perennial; compact, upright to outwardly spreading and mounded plant habit; strong and freely branching growth habit with numerous lateral branches, dense and bushy appearance; vigorous growth habit; medium growth rate.

*Plant height*.—About 40 cm to 50 cm.

*Plant width*.—About 40 cm to 50 cm.

*Lateral branches (peduncles)*.—Length: About 10 cm to 25 cm. Diameter: About 4 mm to 6 mm. Internode length: About 1 cm to 2.5 cm. Angle: Upright to outwardly spreading. Strength: Strong. Texture: Pubescent, rough. Color: Close to 144A; spots, close to 200A.

Leaf description:

*Arrangement*.—Basal leaves, typically opposite and cauline leaves, typically alternate; simple; sessile.

*Length*.—About 7 cm to 15 cm.

*Width*.—About 2.5 cm to 4.5 cm.

*Shape*.—Oblanceolate to obovate.

*Apex*.—Acute.

*Base*.—Attenuate to acute.

*Margin*.—Dentate; undulate.

*Texture, upper and lower surfaces*.—Pubescent; rough.

*Venation pattern*.—Pinnate.

*Color*.—Developing and fully expanded leaves, upper surface: Close to 137A; venation, close to 145B. Developing and fully expanded leaves, lower surface: Close to 137C; venation, close to 138B.

Inflorescence description:

*Type and arrangement*.—Single-type inflorescence form with elliptic-shaped ray florets and tubular disc florets; inflorescences borne on terminal and axillary peduncles above and beyond the foliar plane on strong peduncles; ray and disc florets arranged acropetally on a capitulum.

*Fragrance*.—None detected.

*Flowering season*.—Plants begin flowering about ten weeks after planting; long flowering period, plants flower continuously from mid-July until the end of October in The Netherlands.

*Inflorescence longevity*.—Good postproduction longevity with inflorescences lasting about eight to ten weeks on the plant; inflorescences persistent.

*Quantity of inflorescences*.—Freely flowering habit, typically more than 50 inflorescences developing per plant during the flowering season.

*Inflorescence buds*.—Height: About 1 cm to 2 cm. Diameter: About 1 cm to 2 cm. Shape: Round. Color: Close to 145A.

*Inflorescences*.—Diameter: About 5 cm to 8 cm. Depth (height): About 3 cm to 4 cm. Diameter of disc: About 1.5 cm to 2.5 cm. Receptacle height: About 1 cm to 2 cm. Receptacle diameter: About 7 mm to 12 mm.

*Ray florets*.—Number of ray florets per inflorescence: About 14 to 18 arranged in a single whorl. Length: About 3 cm to 4 cm. Width: About 1 cm to 1.5 cm. Shape: Elliptic. Apex: Emarginate. Base: Acute. Margin: Entire. Texture, upper surface: Smooth, glabrous. Texture, lower surface: Rough, glabrous. Color: When opening, upper surface: Close to 14A; apex, close to between 183A and 200A. When opening, lower surface: Close to 1B tinged with close to between 183A and 200A. Fully opened, upper surface: Ground color, close to 13A; mid-section towards the base and at the apex, overlain with close to between 183A and 200A; color does not change with development. Fully opened, lower surface: Close to 6A; at the apex, close to between 183A and 200A; venation, close to 145A.

*Disc florets*.—Arrangement: Numerous disc florets massed at center of receptacle. Length: About 1 cm to 3 cm. Width: About 1 mm to 2 mm. Shape: Tubular, elongated. Apex: Obtuse. Color: Apex: Initially, close to 77C and becoming closer to 200A with development. Mid-section: Close to 200B. Base: Close to 200A.

*Phyllaries*.—Number of phyllaries per inflorescence: About 20 to 30 in about three whorls. Length: About 1.5 cm to 2 cm. Width: About 3 mm to 7 mm. Shape: Lanceolate. Apex: Acute. Base: Fused. Margin: Entire. Texture, upper and lower surfaces: Rough, pubescent. Color, upper surface: Close to 143A. Color, lower surface: Close to 143C.

*Reproductive organs*.—Androecium (present on ray and disc florets): Quantity per floret: One per floret. Filament length: About 1 mm to 2 mm. Filament color: Close to 200B. Anther shape: Round. Anther length: About 1 mm to 2 mm. Anther color: Close to 200B. Pollen amount: Abundant. Pollen color: Close to 12A. Gynoecium (present only on disc florets): Quantity per floret: One per floret. Pistil length: About 2 mm to 3 mm. Stigma shape: Two-parted. Stigma color: Close to 200C. Style length: About 1 mm to 2 mm. Style color: Close to 200C.

*Seeds and fruits*.—Seed and fruit production has not been observed on plants of the new *Rudbeckia*.

Disease & pest resistance: Plants of the new *Rudbeckia* have been observed to be resistant to Powdery Mildew (*Oidium* sp. or *Sphaerotheca fuliginea*). Resistance to pests and other pathogens common to *Rudbeckia* plants has not been observed on plants of the new *Rudbeckia*.

Garden performance: Plants of the new *Rudbeckia* have been observed to have good garden performance and to tolerate wind, rain and temperatures from about −20° C. to about 40° C.

It is claimed:

1. A new and distinct *Rudbeckia* plant named 'ET RDB 401' as illustrated and described.

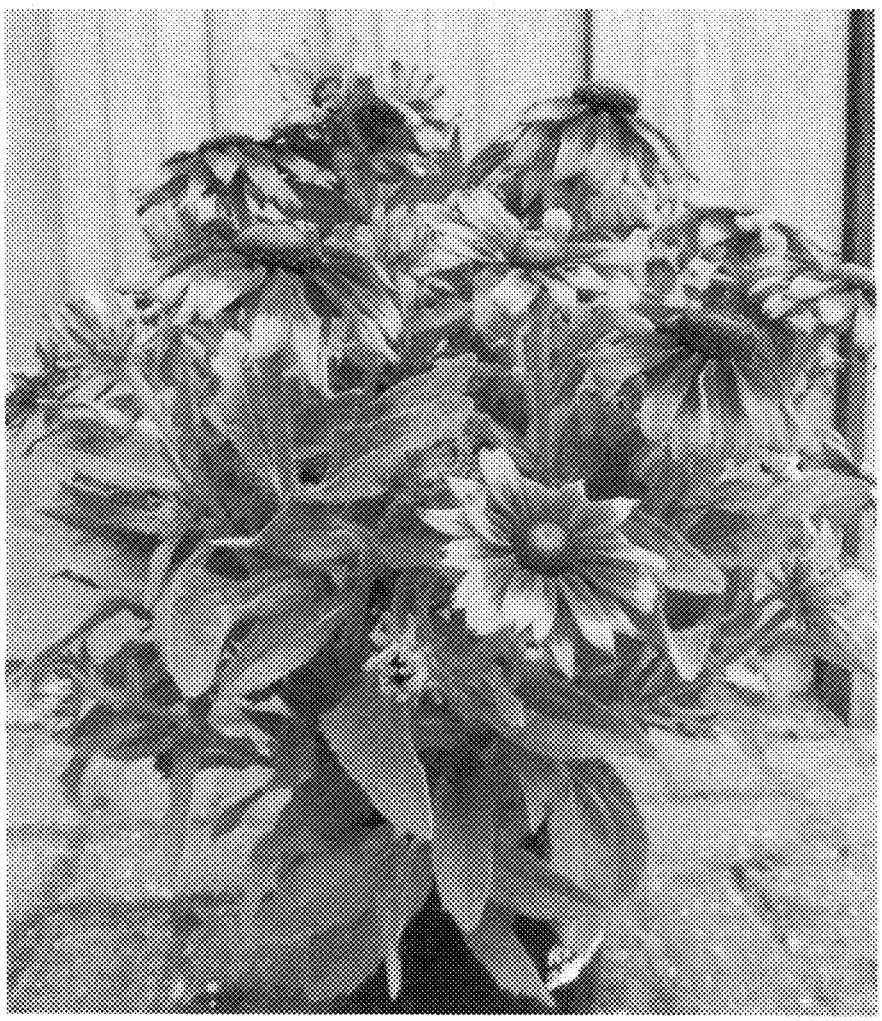

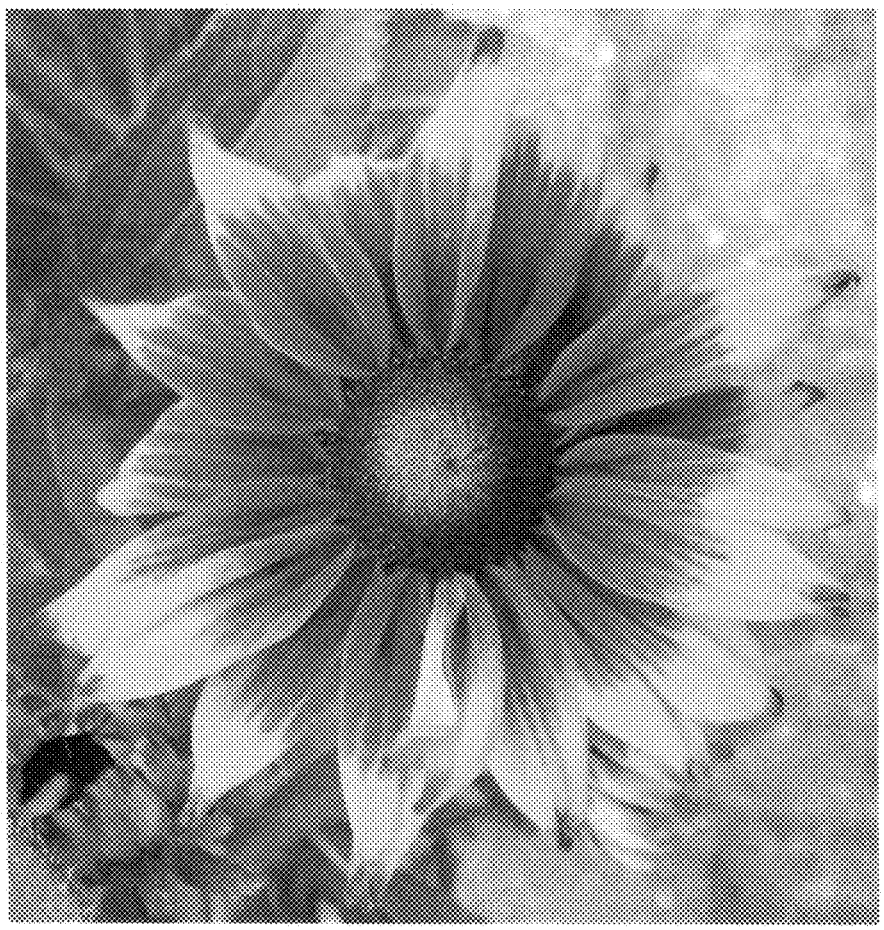

* * * * *